United States Patent [19]

Iskra

[11] Patent Number: 4,605,402
[45] Date of Patent: * Aug. 12, 1986

[54] SOFTENING OF A COMPOSITE ABSORBENT PRODUCT

[75] Inventor: Michael J. Iskra, Flemington, N.J.

[73] Assignee: Personal Products Company, Milltown, N.J.

[*] Notice: The portion of the term of this patent subsequent to Dec. 17, 2002 has been disclaimed.

[21] Appl. No.: 641,549

[22] Filed: Aug. 17, 1984

[51] Int. Cl.⁴ ............................................. A61F 13/16
[52] U.S. Cl. ..................................................... 604/368
[58] Field of Search ................ 604/367, 368, 380–383, 604/385, 374, 375, 378, 379

[56] References Cited

U.S. PATENT DOCUMENTS

| Re. 26,151 | 1/1967 | Duncan et al. | 604/379 |
| 2,788,003 | 4/1957 | Morin | 604/379 |
| 4,102,340 | 7/1978 | Mesek et al. | 604/379 |
| 4,186,165 | 1/1980 | Aberson et al. | 604/379 |
| 4,340,057 | 7/1982 | Bloch et al. | 604/379 |
| 4,500,315 | 2/1985 | Pieniak et al. | 604/379 |

*Primary Examiner*—John D. Yasko
*Attorney, Agent, or Firm*—Martha A. Michaels

[57] ABSTRACT

A softened, absorbent, composite structure is provided which structure is comprised of a fibrous web containing at least about 200 percent by weight of superabsorbent and containing a wicking layer subjected to microcorrugating in at least one direction and perfembossing to yield an absorbent composite structure having a Taber stiffness value less than about 25, preferably less than about 10.

10 Claims, 10 Drawing Figures

SOFTENING OF A COMPOSITE ABSORBENT PRODUCT

BACKGROUND OF THE INVENTION

The present invention relates to new and improved thin, soft, absorbent products and more particularly to new and improved soft compressed composites incorporating superabsorbent material and which composites absorb large quantities of liquids.

Disposable absorbent products have been known for some time, including such products as disposable diapers, sanitary napkins, wound dressings, bandages, incontinent pads, and the like. These products incorporate an absorbent batt which is used to absorb and hold or contain body fluids. Initially, in many of these products, especially diapers and sanitary napkins, the absorbent batt comprised what is termed "wadding" or plies of tissue. The wadding was disposed between an impermeable backing and a permeable facing and the plies of tissue were used to absorb and, hopefully, contain the liquid within the product. A diaper which utilizes such an absorbent batt is disclosed in U.S. Pat. No. Re. 26,151.

The wadding type of batt was replaced, for the most part, by an improved absorbent batt which comprises what is termed "fluffed wood pulp fibers". This absorbent batt comprises a layer of individualized wood pulp fibers with the layer having substantial thickness. A diaper which incorporates such a fluffed wood pulp absorbent batt is described in U.S. Pat. No. 2,788,003. This diaper had improved absorbent capacity and somewhat better containment than a diaper using a wadding layer. Also the fluffed wood pulp layer is quite soft, flexible and conformable and hence, produces an improved diaper over diapers using wadding as the absorbent layer.

Though the fluffed wood pulp absorbent batts have improved capacity, the efficiency with which the capacity is used in a diaper or sanitary napkin is poor. The reason for this, is that the fluid to be absorbed is generally deposited in a localized area within the absorbent batt and the ability for the fluid to move along the plane of the batt is poor. The fluid follows the path of least resistance and consequently moves to the closest edge of the batt where it generally is no longer contained and the product leaks. Furthermore, the wood pulp batts lack stability, e.g., when a diaper is being worn, the batt tends to break up creating bunching.

U.S. Pat. No. 3,017,304 discloses an absorbent product which incorporates in the product a densified, paper-like layer. This paper-like layer acts as a wick, i.e., liquid which is placed on the layer tends to move rapidly along the plane of the layer. When incorporated in combination with fluffed wood pulp fiber, the resultant product uses the absorbent capacity of the fluffed wood pulp much more efficiently. Diapers which incorporate this paperlike layer combined with fuffed wood pulp are disclosed and described in U. S. Pat. Nos. 3,612,055 and 3,938,522. This concept of combining a wicking or capillary skin or layer with fluffed wood pulp fibers has gained wide acceptance in many absorbent products including disposable diapers and sanitary napkins. Even though these products make much greater use of the capacity of the absorbent batt, they still do not totally contain the absorbed liquid. It is probable that these products will leak before the full capacity of the batt is used for absorption. This is especially true if pressure is placed on the batt while wet, for example a baby sitting down on a previously wetted diaper will very often cause the batt to leak. Although the batt is somewhat stabilized by the paper-like densified skin, it may crack and separate.

Recently, elastic leg diapers or stretch diapers have been introduced into the marketplace. Though these diapers provide no better absorbent batt than flat diapers or the prior art diapers, they have indicated improved containment of liquid. Such diapers are disclosed and described in U.S. Pat. Nos. 3,860,003, 4,050,462, and 4,324,245. Though the containment features are better than the prior art products, the elasticized products fit more tightly permitting less air circulation. Frequently, this can become irritating to the skin and the tighter the elastic or the more close fitting the diaper, the greater the irritation. This is especially true adjacent the area where the elastic leg portion of the product contacts the wearer.

A number of years ago "superabsorbent materials", i.e., materials which will absorb many times their weight of liquid, were developed. Since the development of such materials, people have been trying to incorporate them in absorbent products such as diapers and sanitary napkins to enhance the absorptive performance of these products. Theoretically, a minimum amount of superabsorbent incorporated in a product would make that product perform as well or better than the prior art products. Perhaps one of the first products to incorporate such a superabsorbent material in a disposable diaper is disclosed in U.S. Pat. No. 3,670,731. This patent discloses an absorbent dressing comprising an absorbent layer sandwiched between a permeable facing and an impermeable backing sheet. The absorbent layer contains water insoluble cross-linked hydrocolloid polymer as the superabsorbent material.

Even though superabsorbent materials have been available for some time, they have not gained wide acceptance in absorbent products such as disposable diapers and sanitary napkins. A primary reason for this lack of acceptance of the superabsorbents is failure to develop a product capable of economically utilizing the highly increased absorptive capacity of the superabsorbent materal. In order to economically utilize a superabsorbent, the liquid being absorbed must be transported to the superabsorbent material. In other words, the superabsorbent material must be placed in contact with the liquid. Furthermore, as the superabsorbent material absorbs the liquid, it must be allowed to swell. If the superabsorbent is prevented from swelling, it will cease absorbing liquid. Hence if the superabsorbent material is to function in diapers and sanitary napkins wherein the liquid to be absorbed is placed in a small void area, the structure of the absorbent layer containing superabsorbent materials appears to be critical. Over the years a number of techniques have been disclosed in an attempt to provide structures which make efficient use of the superabsorbent material. Such products are disclosed in U.S. Pat. Nos. 4,103,062, 4,102,340, and 4,235,237. In addition, methods for incorporating superabsorbents into suitable layers or suitable configurations which can be placed in an absorbent product, are disclosed in U.S. Pat. Nos. 4,186,165, 4,340,057 and 4,364,992. To date, none of these products has met with any substantial commercial success.

In copending appplication Ser. No. 439,963 filed Nov. 8, 1982, a particularly useful compressed composite is formed. This application is hereby incorporated by reference. The compressed composite product is preferably made from a nonwoven fabric such as polyester. The fabric has associated with it at least 200 percent by weight of superabsorbent to form an absorbing layer. In order to provided a product which will not only absorb liquid but also transport liquid, wood pulp fibers or other suitable wicking materials are cast in a layer on at least one side of the absorbing layer. The product is then compressed to yield a very high liquid absorbing product. However, the resulting compressed composite is quite stiff, and hence requires softening to provide flexibility for utilization in products such as diapers and the like. The flexibility provided needs to be permanent, i.e. the surrounding environment, handling of the product and its subsequent use will not affect the softness and flexibility.

The present invention provides a new and improved absorbent composite structure which utilizes a substantial portion of the absorptive capacity of superabsorbent materials and yet is soft and flexible. This soft, flexible composite is substantially completely stable and retains its stable state even though rendered soft and flexible. Whether wet or dry the composite does not break, bunch or separate. The soft composite retains absorbed liquid without yielding any of the liquid when the composite is under pressure.

SUMMARY OF THE INVENTION

The present invention provides an absorbent composite product structure which is comprised of a fibrous web superabsorbent and other materials suitable for wicking liquid. The fibrous web contains the superabsorbent disposed in amongst the fibers of the web in an amount of at least 200 percent by weight based on the web weight. A wicking layer is formed of suitable wicking materials such as wood pulp fibers and is placed on the fibrous web and the two layers are compressed to yield a compressed composite structure. The absorbent composite structure is rendered flexible to possess a Taber stiffness value of about 25 or less.

The fibrous web used as a basis for the absorbing layer of the compressed composite structure is preferably a low density resilient fibrous web consisting of randomly disposed fibers which result in a web having a dry bulk recovery of at least 30 percent and initial dry bulk of at least 20 cc/gram, a wet bulk of at least 30 cc/gram, and a weight less than about 4 oz/yd$^2$, preferably less than about 3 oz/yd$^2$. The fibrous web is used to spacially distribute superabsorbent material so that upon exposure to an aqueous fluid, swelling occurs with minimal interference from adjacent superabsorbent material. After formation of the absorbing layer, the wicking layer is formed as a superposed layer on the absorbing layer. The wicking layer generally is a layer of wood pulp fibers in an amount of about 4 oz/yd$^2$ or more. The two layers, while still in a moist state of at least about 10 percent moisture are compressed to form a compressed composite product. The resulting compressed composite is too stiff for most uses due to the high loading of superabsorbent in the absorbing layer. It has been discovered that this compressed composite product can be softened to a Taber stiffness of about 25 or less.

The present invention further provides a method for preparing a soft, flexible, absorbent composite structure. The compressed composite product discussed heretofore is first subjected to microcorrugating and then to perf-embossing. The microcorrugating process consists of passing the web through fluted intermeshing rolls having sufficient pressure to fracture the superabsorbent and form cross-directional hinge lines The perf-embossing is carried out by known techniques such as that exemplified in U.S. Pat No. 3,817,827. In order for the absorbent composite structure to be softened and reduced substantially in Taber stiffness it is necessary to attain the glass transition temperature of the superabsorbent material so that the superabsorbent polymer is brittle and can be reduced in size effectively by the mechanical working and crushing provided by the microcorrugating and the perf-embossing. The glass transition temperature is reached by reducing the moisture content sufficiently to permit satisfactory operation at the temperature of the room in which the operating is being carried out. For most superabsorbent materials the satisfactory moisture content is less than about 10% by weight of moisture of the absorbent composite structure.

In the microcorrugating process step, a Taber stiffness is reduced by at least 50% and frequently by at least 70%. During the subsequent perf-embossing step, the Taber stiffness is reduced to a value generally less than 15 but in each instance to a value less than 25. The perf embossing should provide sufficient impact points on the product to further reduce the superabsorbent polymer particle size. Generally, if the impact points are no more than ¼ inch apart and are somewhat continuous, a satisfactory change in Taber stiffness value will be achieved. In the process of perf-embossing, the composite is passed through a pair of rolls which have knuckles and which intermesh to shear the composite structure in the desired fashion. When looking at the structure after it has been perf-embossed, there are raised areas produced by lower knuckles and depressions produced by upper knuckles. If the structure is viewed from the other side, the raised areas become depressions and the depressions become raised areas. The depressions are densified regions which hold and wick liquid. Interconnecting the raised areas and the depressions are intermediate portions which have received most of the mechanical working which reduces the superabsorbent polymer size and fuses the layers of the composite together in the shear areas. At locations where the upper knuckles pass very close to the lower knuckles of the rolls, the work applied to the structure exceeds the strength of the structure and produces apertures in it. The length of the apertures can be varied by controlling the overlap of the upper knuckles and lower knuckles or the size of the knuckles of the rolls. Though the flexibility of the structure is increased by the apertures, the overall strength of the product may be decreased. Therefore, the preferred product of the present invention employs controlled portions of both apertures and partially fractured or sheared regions.

BRIEF DESCRIPTION OF THE DRAWINGS

Referring now to the drawings, FIG. 1 represents a perspective view of starting material utilized to make the compressed composite product which is softened in the present invention. The starting material 10 is a fibrous web 12 containing at least about 200 percent superabsorbent by weight of the web. The superabsorbent material 16 is distributed throughout the fibrous web 12. A wicking layer 14 is placed on each side of the fibrous web 12. The wicking layer generally is wood pulp fibers. When the product is compressed, a transition zone 18 is formed at the junction of each side of the absorbing layer, i.e., fibrous web 12 with the wicking layers 14.

FIG. 2 denotes a section of the product of FIG. 1 which has a fibrous web as an absorbing layer 22. Interspersed among the absorbing layer fibers 23 is superabsorbent material 24. Immediately associated with the absorbing layer is the wicking layer 28. Some portions of the wicking layer fibers 26 extend into and become intregal with the absorbing layer 22. Thus forming a transition zone 25. By "integral web" is meant in intimate contact with but not requiring physical or chemical bonding. The structure depicted in FIG. 2A is a compressed version of FIG. 2. Upon compression, some of the portions in the wicking layer 28 will extend into and become integral with the fibers of the absorbing layer 22. These wicking layer portions will also be in contact with the superabsorbent material 24. Generally at least 10% moisture is present when the structure is compressed under a pressure sufficient to compact the structure and cause the softened surface of the superabsorbent material to provide the necessary adhesion to the fibers of the absorbing layer so that the composite remains in a compacted state even when dry.

FIG. 3 is a perspective view of an absorbent composite structure of the present invention namely that of FIG. 2A which has been microcorrugated. The structure 30 contains a wicking layer 32, an absorbing layer 34 and microcorrugation hinge lines 36 and 38 which provide a Taber stiffness of about 25 or less.

FIG. 4 is a perspective view of an absorbent composite structure which after microcorrugating has been perf-embossed in accordance with the present invention. The composite 40 contains a wicking layer 44 and an absorbing layer 42. Following the microcorrugating and the perf embossing, hinge lines 46 and apertures 49 are placed in the structure providing a pattern as shown. The Taber stiffness of the product is at least 75% less than that of the product prior to treatment and in most instances is less than 15.

FIG. 5 depicts a disposable diaper 50 utilizing an absorbent composite structure of the present invention. A portion of the drawing is broken away for clarification. The disposable diaper 50 has a liquid-permeable facing 56 and a liquid-impermeable backing 52. In between the facing 56 and the backing 52 is an absorbent composite structure 54. The diaper 50 is laminated into unitary form by glue lines 58. It is provided with tape tabs 59 for securing the diaper product 50 about the waist of the wearer.

FIG. 6 is a perspective view of a sanitary napkin 60. The napkin is comprised of a liquid-impermeable shell 64 which contains an absorbent composite structure 66 and is covered over the upper surface with a liquid-permeable facing 62. The absorbent structure 66 is made in accordance with the present invention and is similar to that of FIG. 4.

FIG. 7 is an enlarged side elevational view of a portion of the embodiment shown in FIG. 3. The portion 70 is comprised of an absorbing layer 74 and wicking layers 72. The microcorrugating has provided hinge lines at 76.

FIG. 8 is an enlarged side elevational view of a portion of the microcorrugating rolls 82 and 84. The rolls are provided with intermeshing flutes 86 and 88. These flutes provide the hinge lines heretofore mentioned.

FIG. 9 is a graph depicting the test results of an example. The test performed on the control sample and the samples prepared in accordance with the present invention is derived from the GAT apparatus described and set forth in U.S. Pat. No. 4,357,827 issued Nov. 9, 1982. The values given show the absorbency of a simulated urine solution under a load of 0.5 psi in different periods of time. The absorbency value is what the structure can absorb in the given time while the structure is under a load of 0.5 psi. The values given in FIG. 9 will be discussed in the example.

Figure 1:
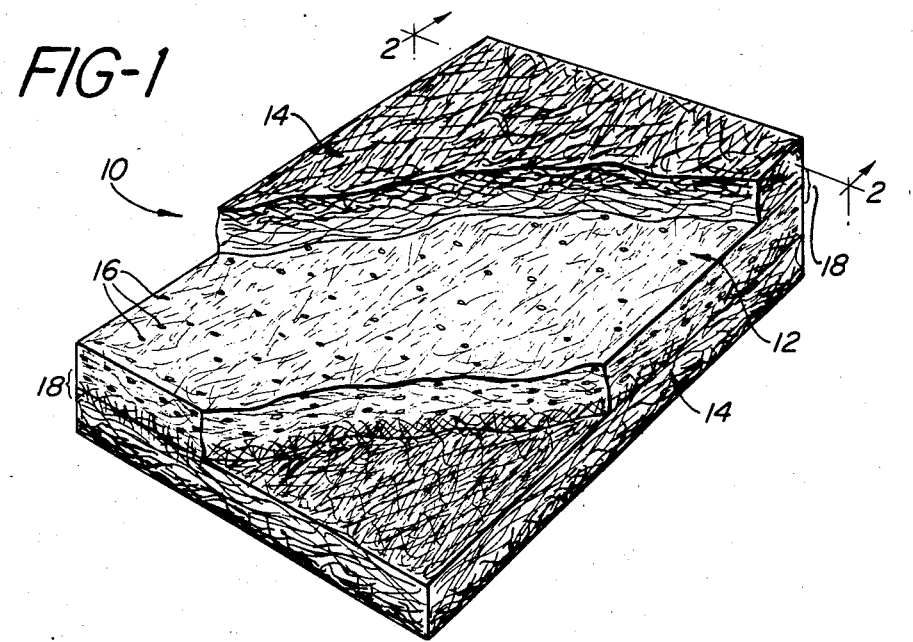
FIG. 1 is a perspective view illustrating one type of starting material for the present invention.
Figure 2:
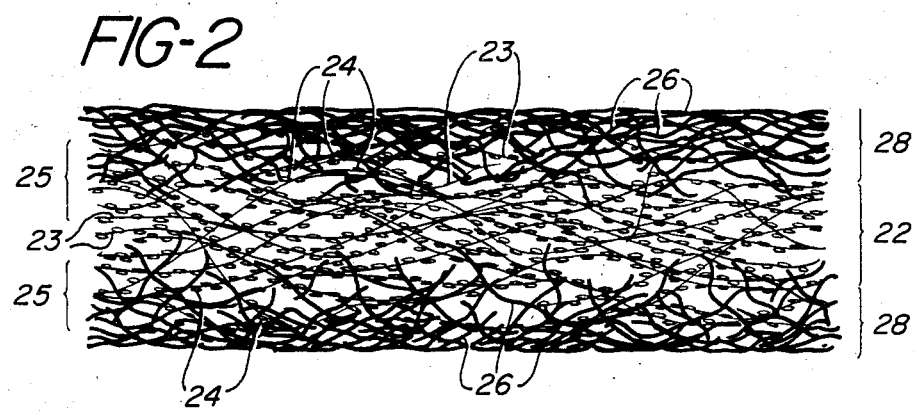
FIG. 2 is an enlarged cross-sectional view of FIG. 1 taken along line 2—2.
Figure 2A:
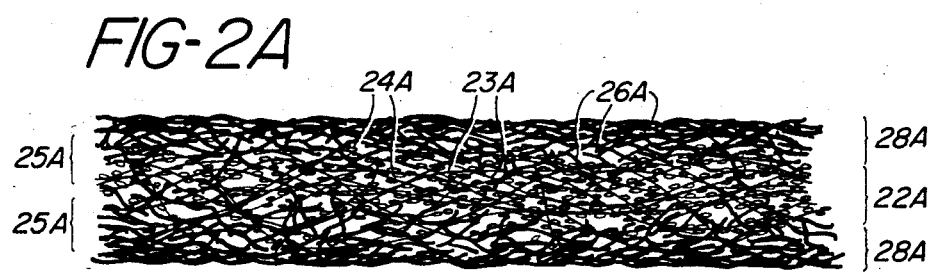
FIG. 2A is a cross-sectional view as in FIG. 2 after compression of the product.
Figure 3:
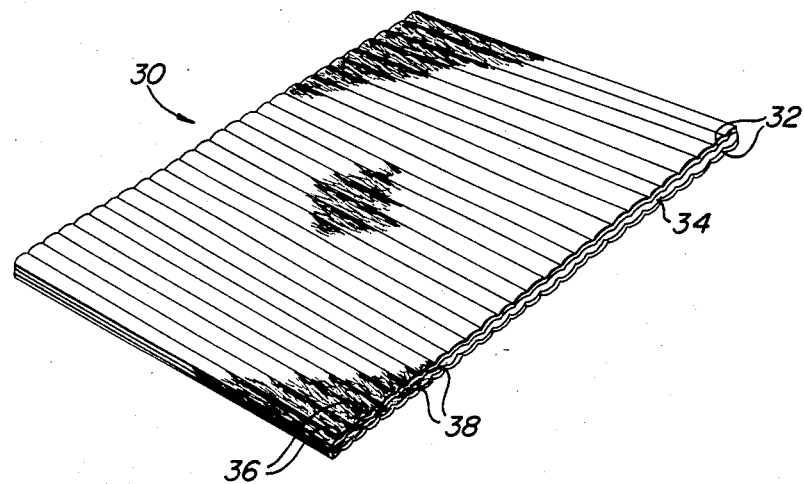
FIG. 3 is a perspective view of the product after the microcorrugating step.
Figure 4:
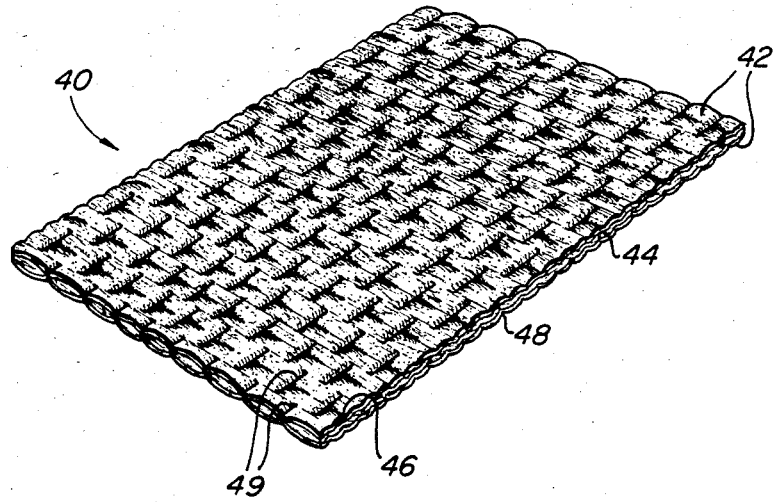
FIG. 4 is a perspective view of one embodiment of the present invention.
Figure 5:
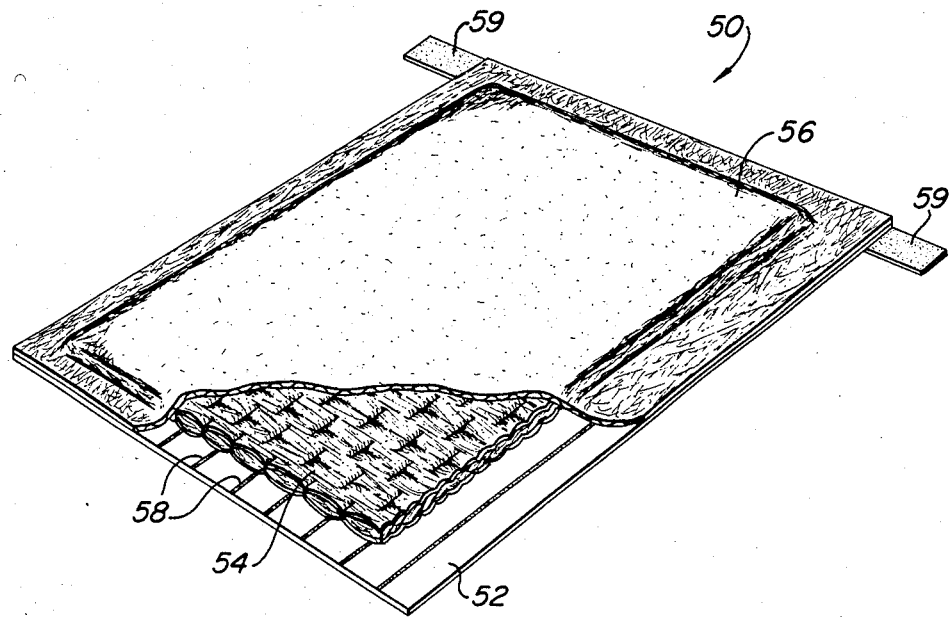
FIG. 5 is a perspective view of one embodiment of the present invention with a portion broken away for clarity.
Figure 6:
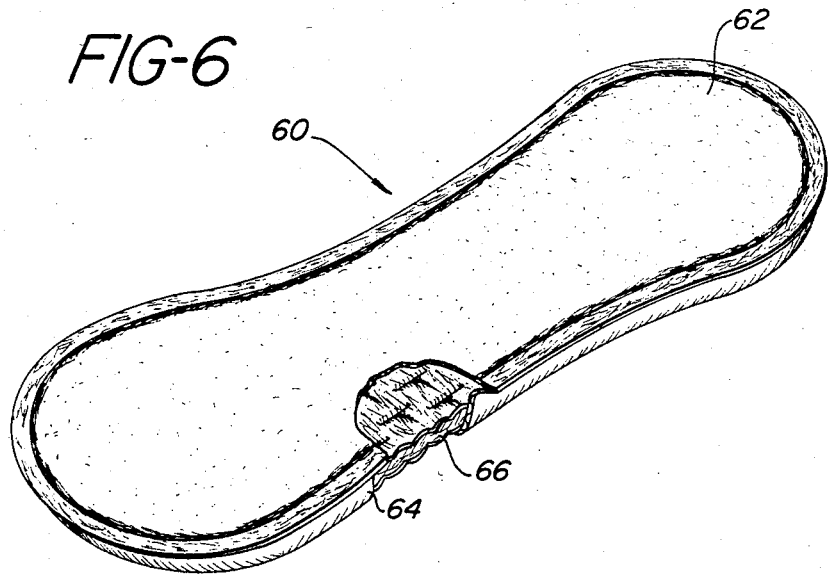
FIG. 6 is a perspective view of a further embodiment of the present invention with a portion broken away for clarity.
Figure 7:
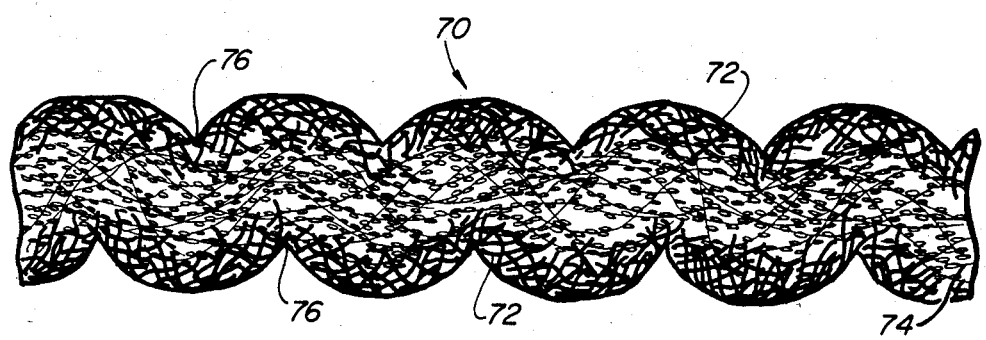
FIG. 7 is an enlarged side elevational view of a portion of the embodiment shown in FIG. 3.
Figure 8:
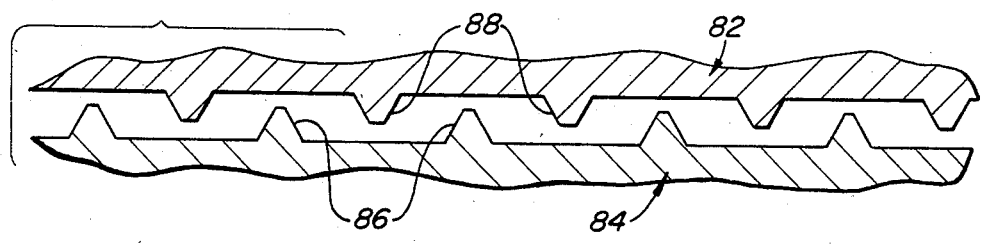
FIG. 8 is an enlarged side elevational view of a portion of the microcorrugating rolls.

The products depicted in the drawings and other products such as incontinent pads, wound dressings and the like may be made from the absorbent composite structure of the present invention.

The fibrous web which contains the superabsorbent and forms the basic absorbing layer for the absorbent composite of the present invention is of substantially high loft and upon dry compression followed by a release has a tendency to return substantially to its original thickness. For instance, fibrous webs formed from synthetic staple fibers, such as polyethylene, polypropylene, polyester, nylon, bicomponent fibers, and the like, are particularly desirable. Melt blown fibrous webs also are suitable. Generally, the fibers are air-laid or melt blown to form a web which if needed is then stabilized. Stabilization may be achieved by heat-through bonding, adhesive bonding, point embossing with heat or adhesive, and the like. The stabilizing process is selected according to the fibers used and the process used to form the web. Suitable procedures for forming a web include carding, wet-laying, air-laying, or combinations of these, melt blowing and other suitable known techniques. The fibrous web preferably has a dry bulk recovery of at least about 30 percent and an initial dry bulk of at least 20 cc/gm and a wet bulk of at least about 30 cc/gm. The fibrous web generally has a weight less than about 4 oz/sq. yd., preferably less than about 3 oz/sq. yd.

A wicking layer generally of wood pulp fibers is placed on at least one side of the superabsorbent containing fibrous web and in the presence of about 10 percent moisture or more, the product is compressed. The resulting compressed composite generally possesses a Taber stiffness in the machine direction of at least about 130 and sometimes as high as 350.

The superabsorbent material present in an intermittently dispersed form in the absorbing layer is generally a water-insoluble but water-swellable polymeric substance capable of absorbing water in an amount which is at least 10 times the weight of the substance in this dry form. The superabsorbent material is in the form of particles which may be in the shape of fibers, spheres, bits of film, globules, or the like, or may be applied in the form of a liquid monomer solution which is subsequently polymerized Generally, the polymerized monomer solution provides globules and bits of film-like particles in the structure.

In one type of superabsorbent material, the particles or fibers may be described chemically as having a backbone of natural or synthetic polymers with hydrophilic groups or polymers containing hydrophilic groups being chemically bonded to the backbone or an intimate admixture therewith. Included in this class of materials are such modified natural and regenerated polymers as polysaccharides including, for example, cellulose and starch and regenerated cellulose which are modified by being carboxyalkylated, phosphonoalkylated, sulphoalkylated or phosphorylated to render them highly hydrophilic. Such modified polymers may also be cross-linked to improve their water-insolubility.

These same polysaccharides may also serve, for example, as the backbone onto which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain of the general formula

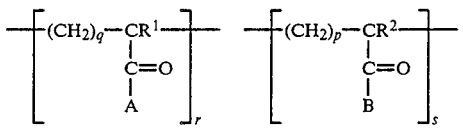

wherein A and B are selected from the group consisting of $-OR^3$, $-O$ (alkali metal), $-OHNH_3$, $-NH_2$, wherein $R^1$, $R^2$ and $R^3$ are selected from the group consisting of hydrogen and alkyl having 1 to 4 or more carbon atoms, wherein r is an integer having a value of 0 to about 5000 or more, s is an integer having a value of 0 to about 5000 or more, r plus s is at least 500, p is an integer having a value of zero or 1 and q is an integer having a value of 1 to 4. The preferred hydrophilic chains are hydrolyzed polyacrylonitrile chains and copolymers of polyacrylamide and polysodium acrylate.

In addition to modified natural and regenerated polymers, the hydrocolloid particle component may comprise wholly synthetic hydrophilic particles. Examples of those now known in the art are polyacrylonitrile fibers which may be modified by grafting moieties thereon such as polyvinyl alcohol chains, polyvinyl alcohol itself, hydrophilic polyurethane, poly(alkyl phosphonates), partially hydrolyzed polyacrylamides (e.g., poly(N-N-dimethyl acrylamide), sulfonated polystyrene, or a class of poly(alkylene oxide). These highly hydrophilic synthetic polymers may be modified by other chemical treatments such as cross-linking or hydrolysis. Further examples known in the art are the non-ionic hydrophilic polymers such as polyoxyethylene, polyoxypropylene and mixtures thereof which have been suitably cross-linked, either chemically or by irradiation. Still another more recent type is a derivative of isobutylene-maleic anhydride copolymer.

Hydrophilic polymers formed from water-soluble acrylate monomers, such as sodium, potassium, ammonium (or combination of cations), acrylate, may be placed on the absorbing layer by spraying or otherwise placing a solution thereon follwed by polymerization and cross-linking, for example, by irradiation.

In addition, naturally occurring materials such as gums, may be used. For instance, guar gum is suitable.

The superabsorbent material is combined with the fibrous web by any means suitable to distribute the superabsorbent material therein trying to minimize interference by one superabsorbent entity with another upon the swelling of the first. If the superabsorbent material is a powder it may be sprinkled onto the fibrous web either in dry form or the web may be moistened. If the superabsorbent is in granular form it may be desirable to slightly moisten the superabsorbent before placing it in contact with the web. The superabsorbent material will contain particles which range in size from about 0.005 mm in diameter to globules that are continuous along fibers for a distance up to several inches.

Another method of placing the superabsorbent in the web is spraying a monomer solution on the web or saturating the web with a monomer solution followed by polymerization of the monomer. One typical way to polymerize the monomer is by use of irradiation. It is desirable to place the superabsorbent somewhat evenly throughout the fibrous web. However, even if the superabsorbent is powderlike and in the form of a layer, it tends to function better than such a layer has in previously known products. It may be desirable to place more superabsorbent in one area than in another and/or to place the superabsorbent in the structure in predetermined patterns.

Any superabsorbent which absorbs large amounts of liquids is suitable for use in the absorbing layer of the present invention.

As mentioned heretofore, the compressed composite containing the superabsorbent tends to be stiff and substantially non-flexible. Since the end uses of the fibrous web require that the web be soft, flexible and pliable, it has been discovered that microcorrugating and perf embossing of the composite provides the necessary reduction in stiffness without damaging the properties of the composite, which are desirable for its end use. Frequently, the Taber stiffness of the composite wherein the absorbent layer contains at least 200 percent superabsorbent exceeds 300 Taber stiffness in the machine direction. In the cross-direction the Taber stiffness generally exceeds 70. In order to have a product satisfactory for use in disposable products such as diapers and sanitary napkins, it is necessary to reduce the Taber stiffness value to about 25 or preferably 15 or less in at least one direction. The Taber stiffness value is obtained in accordance with the procedure found at ASTM D 2969 and is expressed herein as gm/lineal cm.

The wicking layer is comprised of hydrophilic fibers, such as rayon fibers, cellulosic fibers, peat moss, acrylic fibers, or mixtures thereof. The cellulosic fibers include wood pulp fibers, cotton linters, and the like. The wood pulp fibers generally are those that are used to form the fluff or fibrous batt layer in conventional absorbent products such as disposable diapers, sanitary napkins, etc. Other cellulosic fibers that might be used are rayon fibers, flax, hemp, jute, ramie, cotton and the like. The fibers or peat moss or mixtures thereof are placed in such a way as to form a layer in which the particles are close to one another so as to provide a higher capillary pressure to promote wicking of liquid in the plane of the layer.

What appears to be only a small difference in capillary pressure is all that is required for one layer to attract and drain liquid from an adjacent layer. The force causing a liquid to enter a cylindrical capillary is expressed by the equation:

$$P = \frac{(2 \cos \theta)}{r}$$

wherein the force is represented by the capillary pressure and

P is the capillary pressure,
is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is zero) and also increases with narrower capillary radii so that narrower capillaries will draw liquid from wider ones.

The relative wickability between a first fibrous layer and a second layer is affected by both the relative densities of the layers and the relative wettability of the individual fibers in each layer. The individual fibers of the second layer preferably have substantially smaller liquid fiber contact angles than those of the first fibrous layer overcoming the density difference and providing a significant overall increase in capillary pressure to absorb liquid into the second layer.

The fibers of the second layer of fibers (or particles) and/or the density of the layer are selected to create a significant difference in capillary pressure from the first fibrous layer.

The second fibrous (or particle) layer is generally comprised of fibers having a lower liquid-contact angle or wherein the layer is provided with a narrower capillary radii. Examples of such fibers include hydrophilic fibers such as rayon fibers, cellulosic fibers, or peat moss, or mixtures thereof, or the like. Cellulosic fibers include wood pulp fibers, cotton linters and the like.

The wicking layer can be preformed and placed next to the absorbing layer before compression or the wicking layer particles can be air-laid, mechanically entangled therewith, or wet-laid on to the absorbing layer before compression.

The transition zone is a region formed at the junction of the absorbing layer and the wicking layer. Some of the particles, e.g., fibers, of the wicking layer extend into and become integral with the absorbing layer. The region in which the majority of the extending particles lie is identified as the transition zone. In the transition zone, there is a composite of absorbing layer fibers, superabsorbent material, and wicking layer particles. The wicking layer particles which have extended into the absorbing layer are in intimate contact with some of the superabsorbent material of the absorbing layer. This permits the liquid to commence its migration in the z direction to reach the superabsorbent material. As the liquid progresses in the z direction, the superabsorbent material becomes soft and releases the absorbing layer fibers which permit the absorbing layer to return substantially to its uncompressed thickness or more. As the absorbing layer returns to its uncompressed thickness, larger void areas are provided for storage of the liquid and for increased swelling of the superabsorbent material as it absorbs the liquid residing in the void areas. The absorbing layer tends to return to its uncompressed thickness or more, probably because of both the resiliency of the fibers and the swelling of the superabsorbent material.

In order for the absorbing layer fibrous web to provide the necessary medium for absorbing liquid, it is preferred that the fibrous web has an initial dry bulk of at least about 20 cc/gm, a dry bulk recovery of at least 30 percent, (preferably 50 percent), a wet bulk of at least about 30 cc/gm, and a weight of less than about 4 oz/yd². The initial dry bulk is the area times thickness of the layer under a load of 0.01 pounds per square inch calculated in cubic centimeters. This value is divided by the weight in grams in order to provide the measurement in cubic centimeters per gram. The dry bulk recovery is obtained by subjecting the web to a load of 1.75 psi for five minutes, removing the load and allowing the web to rest for one minute, subjecting the web to a load of 0.01 psi for one minute and then measuring the final dry bulk while under the 0.01 psi load. The dry bulk recovery is the final bulk divided by the initial bulk expressed in percent. The wet bulk is measured in the same manner as the initial dry bulk except that the web has been saturated with water. It has been found that if the fibrous web is provided with a dry bulk recovery of at least 20 percent (preferably 50%), an initial dry bulk of at least 40 cc/gm, a wet bulk of at least 30 cc/gm, with a web weight of less than 4 oz/yd², the fibrous web can retain superabsorbent material up to at least 1,500 percent of the dry basis weight of the web. It is preferable that the web contain 200 percent to 1,500 percent by weight, dry basis, superabsorbent to the dry basis weight of the web and most preferred is a range from about 400 percent to about 1,200 percent.

The means by which the absorbent composite structure is rendered flexible, pliable and soft according to the present invention is by utilization of one or more mechanical working procedures. The preferred means of mechanical working are microcorrugating and perf embossing in that order. The technique of microcorrugating is disclosed in U.S. Pat. No. 4,116,892 to Schwarz. Although the technique in this patent is identified as one for stretching fibers in order to orient the fibers, the present invention does not wish to stretch but to mechanically work. Schwarz uses his technique to molecularly orient the fibers in a post-molten state. The fibers used in the present invention are already oriented. Thus, additional stretching or further orientation might damage the fibers in the present invention.

It has been discovered that microcorrugating the absorbent structure defined in the present invention puts in hinge lines resulting in a flexible, pliable, soft feel. The rolls described in U.S. Pat. No. 4,116,892 are set with a gap of 0.025 to 0.30 inch in order to break up the superabsorbent particles to a somewhat uniform size and create the desirable hinge lines described heretofore. If the absorbent composite structure of the present invention is simply put through rolls so as to crush the structure, the product actually becomes stiffer and has a high Taber stiffness value. The stretch to the fibers of the absorbent structure is less than 10% when the microcorrugating is performed. It is easiest to pass the compressed composite product through microcorrugating rolls in the machine direction and hence that is the most desirable direction. However, it is acceptable to microcorrugate in the machine direction thereby placing hinge lines in the product in the machine direction. This can be accomplished through rolls with embossing rings which are so placed as to provide the necessary hinge lines. It has been found to be highly desirable to reduce the moisture content of the absorbent composite structure to less than 10% before subjecting it to microcorrugating.

It has been found that when the microcorrugated absorbent composite structure is subjected to perf-embossing after it has been microcorrugated, the absorbent product is a flexible, pliable, soft product which retains substantially its original machine direction strength while having been mechanically worked in such a way as to improve the absorption and reduce the Taber stiffness by a considerable amount, placing the final Taber stiffness below 25, and preferably below 15. The perf embossing is carried out by known techniques such as that exemplified in U.S. Pat. No. 3,817,827. In order for the composite structure to be best treated, it is preferable to attain the glass transition temperature of the superabsorbent material so that the superabsorbent polymer is brittle and can be reduced in size effectively by the mechanical working and shearing provided by the perf embossing. The glass transition temperature is reached by reducing the moisture content sufficiently to permit satisfactory operation at the temperature of the room in which the operation is being carried out. For most superabsorbent materials, the satisfactory moisture content is less than about 10% by weight of moisture of the composite structure.

In addition to the tenderizing, softening and improved flexibility of the absorbent composite structure, it has been noticed that the product absorbs liquid in larger quantities than prior to the mechanical working procedure. Furthermore, the quick absorption of liquid by the product is not substantially decreased. The qualities are particularly beneficial for a compressed composite product used in a disposable diaper. An example of the method of preparing the compressed composite of the present invention is as follows. This example is not intended to be limiting in any way, and extensions and modifications thereof without departure from the spirit and scope of the invention will become apparent from this example.

EXAMPLE

An absorbing layer for a compressed composite is formed of 67 percent polyester fibers and 33 percent bicomponent fibers. The bicomponent fibers have a polyethylene sheath and a polyester core. The web is heat bonded by passing air at a temperature of 350° F. through the web for about one second or less. The resulting web has a weight of 1.2 oz/sq. yd. The web is coated by flooding it with an aqueous solution of sodium acrylate and acrylic acid. The solution contains 38 percent solids. Excess solution is removed from the web and the web is then subjected to electron beam radiation. This electron beam radiation polymerizes the sodium acrylate to polysodium acrylate. The web is repeatedly flooded with liquid, the excess liquid removed, and each time subjected to irradiation until the amount of dry solids add-on of the polysodium acrylate is 10 times the weight of the web.

The polysodium acrylate coated web is passed beneath a hammer mill that deposits wood pulp fibers onto the polyester web. Vacuum is applied under the polyester web so as to lightly compact the wood pulp fibers onto the web. The wood pulp fibers are present in an amount of about 4 oz/sq. yd. per layer and a layer of the wood pulp fibers is deposited on each side of the polyester web. The surface of the pulp layer is sprayed with water so that the total moisture content of the pulp is at least about 10 percent by weight. The total structure is then compressed at a level of 640 psi for 30 seconds. Upon release of the pressure, the pulp has formed into a high density layer with a capillary size suitable for liquid wicking and the resilient fiber layer remains compressed. The product containing about 20 percent moisture has a Taber stiffness in the machine direction of about 343, and in the cross-direction 75. If the compressed composite is subjected to perf embossing at 20 percent moisture, the Taber stiffness in the machine direction increases to about 376 while there is a slight reduction in cross-direction Taber stiffness to a value of about 65. In all instances, the Taber stiffness values are presented in grams per lineal centimeter of the sample.

The compressed composite product containing about 20% moisture is dried to a moisture content of about 3% and subjected to microcorrugating in the machine direction. The rolls are 7 inch cylinders having microcorrugated peaks at 30 dp (diametral pitch) with an engagement of 0.04 inch at a pressure of 290 lbs per lineal inch. These samples, after microcorrugation have a Taber stiffness value of about 27 in the machine direction and 15 in the cross direction. The sample is then subjected to perf-embossing wherein the rolls are set at 0.05 inch engagement with 40 psi. The Taber stiffness of the product which has been microcorrugated and perf-embossed in the machine direction is reduced to 8.0 and in the cross direction to 3.6. It can be clearly seen that the stiffness in the product is reduced by at least 75% in each direction. The mechanically worked product exhibits an improved absorbency in that it shows a 32% increase in absorbency after being mechanically worked.

Figure 9:
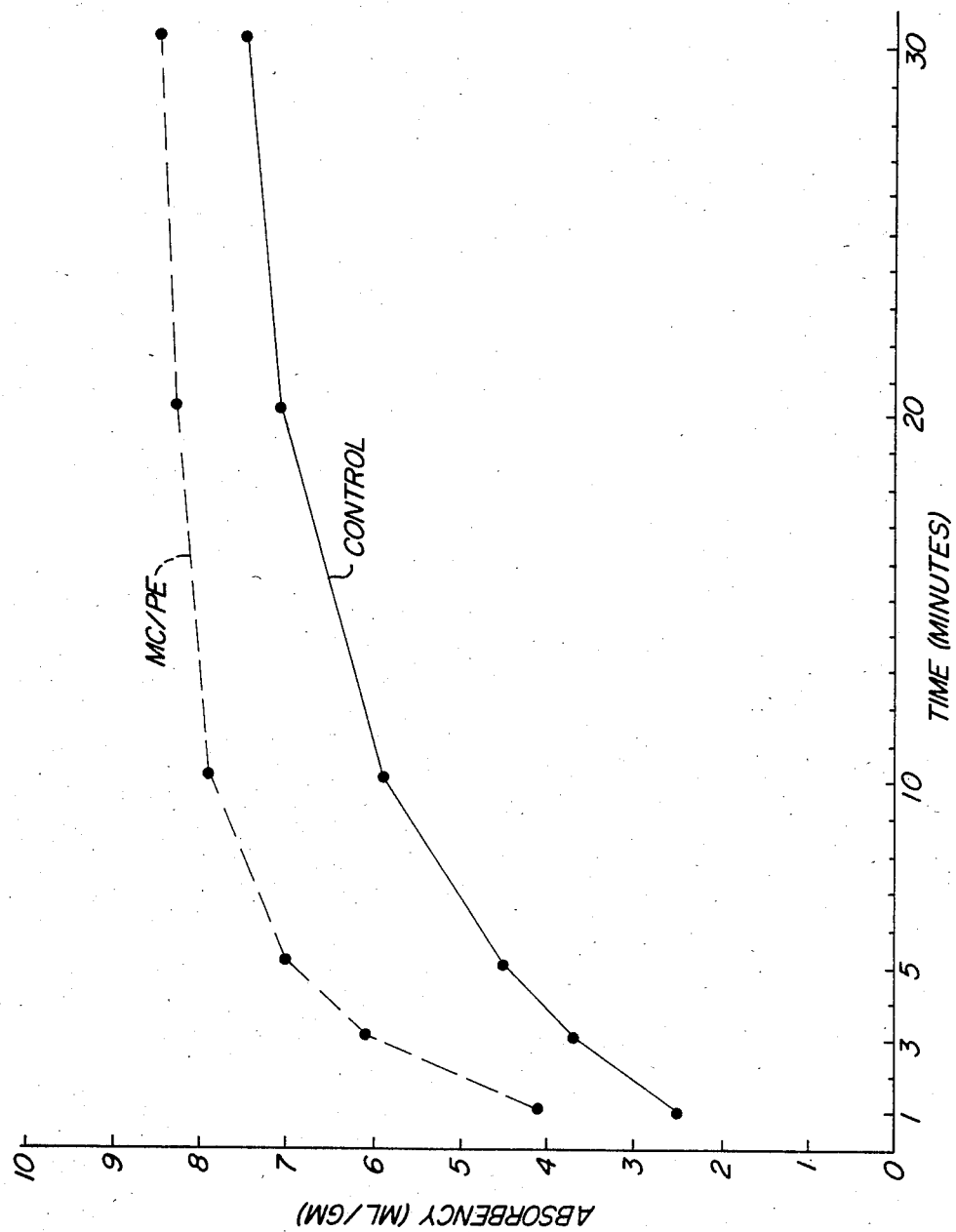
FIG. 9 is a graph depicting the test results of the example.

The results of an absorbency test in given time periods are shown in FIG. 9 in graph form. It is readily seen that the sample treated by microcorrugating and perf-embossing (MC/PE) much more rapidly absorbs liquid in a given time period than an untreated compressed composite product.

From the foregoing it will be observed that numerous variations and modifications may be effected without departing from the true spirit and scope of the novel concept of this invention.

I claim:

1. A microcorrugated, perf-embossed, absorbent composite structure comprising an absorbing layer comprised of a fibrous web having an initial dry bulk of at least about 20 cc/gm., a dry bulk recovery of at least about 30 percent, a wet bulk of at least about 30 cc/gm., and a weight less than about 4 oz/sq. yd., and containing at least about 200 percent superabsorbent and a wicking layer, said structure having a Taber stiffness value less than about 25.

2. The structure of claim 1 wherein the superabsorbent is present in an amount from about 200 percent to about 1500 percent.

3. The structure of claim 2 wherein said superabsorbent is present in an amount from about 400 percent to about 1200 percent.

4. The structure of claim 1 wherein said fibrous web is a polyester nonwoven web.

5. The structure of claim 1 wherein said wicking layer is comprised of wood pulp fibers.

6. The structure of claim 1 wherein said Taber stiffness value is less than about 10.

7. A disposable diaper having an absorbent core comprised of a microcorrugated, perf-embossed composite structure comprising an absorbing layer comprised of a fibrous web having an initial dry bulk of at least about 20 cc/gm., a dry bulk recovery of at least about 30 percent, a wet bulk of at least about 30 cc/gm., and a weight less than about 400 oz/sq. yd., and containing at least about 200 percent superabsorbent and a wicking layer, said structure having a Taber stiffness value less than about 25.

8. A sanitary napkin having an absorbent core comprised of a microcorrugated, perf-embossed composite structure comprising an absorbing layer comprised of a fibrous web having an initial dry bulk of at least about 20 cc/gm., a dry bulk recovery of at least about 30 percent, a web bulk of at least about 30 cc/gm., and a weight less than about 400 oz/sq. yd., and containing at least about 200 percent superabsorbent and a wicking layer, said structure having a Taber stiffness value less than about 25.

9. A method for preparing a flexible, soft, absorbent composite structure which comprises drying an absorbent composite structure to a moisture content less than about 10 percent and subjecting the dried structure to microcorrugating followed by perf-embossing to reduce the Taber stiffness value to less than about 25.

10. The method of claim 9 wherein the Taber stiffness value is reduced to about 10 or less.

* * * * *